United States Patent [19]

Sirany

[11] Patent Number: 5,151,415

[45] Date of Patent: Sep. 29, 1992

[54] METHOD OF TREATING A PAPOVA-TYPE VIRAL INFECTION

[76] Inventor: Dallas Sirany, 5733 Dumas Ave., Minnetonka, Minn. 55345

[21] Appl. No.: 704,452

[22] Filed: May 23, 1991

[51] Int. Cl.⁵ .................... A01N 37/36; A61K 31/61; A61K 31/615

[52] U.S. Cl. .................... 514/163; 514/159; 514/166

[58] Field of Search .............. 514/159, 163, 166; 560/143

[56] References Cited

U.S. PATENT DOCUMENTS

| | | |
|---|---|---|
| 4,055,660 | 10/1977 | Meierhenry ................ 514/535 |
| 4,497,824 | 2/1985 | Schulte ..................... 514/166 |
| 4,956,184 | 9/1990 | Kross ....................... 514/934 |
| 4,987,127 | 1/1991 | Sirany ...................... 514/159 |

OTHER PUBLICATIONS

L. Fry, F. Wojnarowska & P. Shahrad, *Illustrated Encyclopedia of Dermatology* 537-53 (2d ed. 1985).

*Primary Examiner*—Nathan M. Nutter
*Attorney, Agent, or Firm*—Kinney & Lange

[57] ABSTRACT

A method for treating an epithelial tumor of a viral infection involves repeated applications of a paste of acetylsalicylic acid and water to the infection until it is arrested.

27 Claims, No Drawings

METHOD OF TREATING A PAPOVA-TYPE VIRAL INFECTION

BACKGROUND OF THE INVENTION

The present invention relates to the treatment of the papova-type viral infection and in particular to a method and pharmaceutical product for the treatment of warts, including common warts (*verruca vulgaris*) and plantar warts.

Papova viruses are a group of DNA-containing animal viruses that produce epithelial tumors, the best known of which is the common wart (*verruca vulgaris*). Characteristically, the tumor is small, firm and rounded with an elevated horny surface. Depending on the particular type, warts may occur singularly or there may be numerous lesions that coalesce to cover an area. Such lesions are cosmetically undesirous and often can be cosmetically disabling and painful. For example, plantar warts are small, deep seated, firm hyperkeratotic lesions, which are commonly found on the soles, hands and knees. When they are situated on pressure-bearing areas, such as the plantar aspects of the feet, they may be painful and cause difficulty in walking. Plane warts are flesh colored, slightly elevated, polygonal lesions that undersirably intrude upon the face and the back of hands. Finally, genital warts (*condylomata acuminata*) are flesh colored, pedunculated or filiform lesions that occur during the sexually active years and often cause discomfort and irritation in the genital areas.

Warts are a very common viral infection throughout the world that equally affect both sexes. They may be transmitted by either direct or indirect contact and by auto-inoculation. Genital warts are transmitted by sexual contact. Occasionally, some warts will spontaneously resolve within a few months of developing; others, however, persist for years, spreading from one site to another. The average duration of untreated warts is approximately two years. Genital warts, on the other hand, are often resistant to treatment and have a high relapse rate.

Wart treatment methods vary depending on the location and number of the lesions, the degree of associated discomfort and the possibility of cosmetic disability. The success of the treatment varies from method to method. For example, the cytotoxic agent podophyllin used in a 25% solution is used to treat anogenital warts. The podophyllin solution is applied to the infected area and removed about six to eight hours later; Vaseline must be used to protect the surrounding skin. An alternative podophyllin method consists of applying a 15% podophyllin ointment under occlusive plaster to pared periungual warts. This treatment method persists for about six to about eight weeks, with the plaster being changed every three to four days. Neither the 25% podophyllin solution nor the 15% podophyllin ointment can be used on pregnant individuals. Additionally, some patients develop a severe reaction to podophyllin, requiring termination of the treatment.

Cryotherapy, using liquid nitrogen or carbon dioxide snow, is another wart treatment method that is about 70% effective. The duration of freezing depends on the location and size of the wart and can result in some discomfort. If the treatment is successful, the wart usually disappears within two to three weeks; it is not uncommon that repeat treatments are necessary, with longer periods of freezing.

The most common and effective treatment for warts is curettage and cautery. This method, however, is painful and requires local and sometimes general anaesthesia. Surgical removal of warts and radiotherapy, on the other hand, are not recommended. Nitric acid and trichloracetic acid applied with care to pared warts are additional alternative treatments.

Probably the least effective wart treatment involves applications of a salicylic acid solution, ranging in concentration from about 3% to about 10%. Applied daily for about one month, salicylic acid has a low cure rate and usually only succeeds in improving the cosmetic appearance of the wart.

My U.S. Pat. No. 4,987,127, describes the beneficial effects of using acetylsalicylic acid to successfully treat outbreak episodes of herpes simplex and related viruses. Acetylsalicylic acid is a well known drug, available as an over-the-counter pharmaceutical product in the United States. Acetylsalicylic acid is most commonly employed in an ingestible form for analgesic purposes. Acetylsalicylic acid has also been used as a surface supplied analgesic.

The Nitardy patent, U.S. Pat. No. 195,945, suggests the use of acetylsalicylic acid in an ethyl ether and oil base for application to mucous membranes. The patent further suggests a synergistic action between acetylsalicylic acid and ethyl ether.

The Putt patent, U.S. Pat. No. 2,056,208, discloses that acetylsalicylic acid is known for application to mucous membranes of the mouth. The Putt patent also discloses the application of a liniment, including acetylsalicylic acid, to unbroken skin as a liniment for the treatment of inflammation or pain and to provide an analgesic effect. This patent further teaches that in water, acetylsalicylic acid rapidly breaks down to salicylic acid and acetic acid. The rapid breakdown of acetylsalicylic acid is considered undesirable by Putt who suggests the need to use acetylsalicylic acid in a liquid form which does not allow a degradation or breakdown during the time required for absorption through the skin. The particular liniment disclosed is 30 grains in 1 ounce of glycerol oleate or other "unctuous base." The patent further discloses testing for absorption of acetylsalicylic acid by a ferric chloride reaction with any acetylsalicylic present in the urine and by fluorescence of skin which has absorbed acetylsalicylic acid.

The Campbell patent, U.S. Pat. No. 3,119,739, discloses the use of a composition, including acetylmethylsalicylate, for pain relief and as an anodyne agent. The patent includes the statement that "it should be understood in no sense be regarded as a curative agent for the basic cause of the pain." The acetylmethylsalicylate is used as 1-20% mixture in an inert pharmaceutical carrier. Solvents for the acetylmethylsalicylate are preferred as the pharmaceutical carrier but suspensions or emulsions may also be used. Examples of suitable inert pharmaceutical carriers are ethanol, isopropanol and polyethylene glycol. The mixture is useful for treating insect bites and allergic reactions.

The prior art has neither taught nor suggested the use of externally applied acetylsalicylic acid as a treatment for papova-type viral infections, despite prior art disclosing the use of acetylsalicylic acid and related compounds such as methyl salicylate and acetyl methyl salicylic acid as analgesic and anti-inflammatory agents for both internal and external application. To the contrary, the prior art has taught away from pharmaceutical preparations including both acetylsalicylic acid and water because of the fear of rapid degradation of the acetylsalicylic acid component into acetic acid and salicylic acid. Salicylic acid has proven to be an ineffective treatment for epithelial tumors associated with the papova-type virus.

SUMMARY OF THE INVENTION

The present invention is based upon my discovery that a paste of acetylsalicylic acid and water applied to body surface areas infected with papova-type viral epithelial tumors is a highly effective and successful method for completely arresting the virus and permanently eliminating the unsightly and sometimes painful epithelial tumor.

DETAILED DESCRIPTION OF THE PREFERRED EMBODIMENTS

The method of the present invention provides a number of beneficial effects in the treatment of a papova-type viral infection. First, the method completely and effectively eliminates the epithelial tumor caused by the virus without any adverse effects. Second, the method offers a painless nonsurgical alternative for treating the potentially and often painful plantar wart or plantar wart colony. Third, the method eliminates the pain associated with plantar warts.

A pharmaceutical preparation of the present invention is a paste prepared from acetylsalicylic acid and water. Preferably, the paste should be freshly prepared before application. By freshly prepared is meant that paste should be used within about 1 hour of preparation and preferably within 30 minutes and most preferably the first application of paste to the affected region should be made within about 1-5 minutes of preparation of the paste, with the remaining paste used for reapplication during a single treatment period of preferably about 30 minutes. The acetylsalicylic acid used to form the paste may be present as purified powdered acetylsalicylic acid or alternatively as a tablet. Such tablets typically include starch or other tableting agents for holding the acetylsalicylic acid in a tablet form. Although coated or buffered aspirin products may be used to form the powder component of the paste of this invention, they are believed to be somewhat less efficient than traditional aspirin tablets. In all cases, the acetylsalicylic acid should be reduced or ground to a fine powder.

The other major component of the paste is water. Preferably the water is present as distilled water although any potable water such as tap water may be suitably employed to prepare the paste of the present invention. Tap water is believed to be somewhat less efficient than distilled water. Additionally, a low microbial content in the water used in paste formation is believed to be desirable for avoid possible secondary infections in the individual to be treated. The paste is prepared by mixing the powdered acetylsalicylic acid and the water together and stirring vigorously to obtain a stiff, thick and somewhat adherent slurry. Proportions of acetylsalicylic acid to water may be from about 1.63:1.00 to about 0.26:1.00, with proportions of about 0.81:1.00 being preferred. The amount of paste prepared should be adequate to more than cover the affected area.

In one embodiment, a single tablet of about 325 milligrams (about 5 grains) of acetylsalicylic acid was crushed and then reduced by grinding to a fine powder. Approximately 0.40 milliliters of distilled water was added to the powder and the resulting powder and liquid mixture stirred until fully blended, for about 1 minute, to obtain a stiff paste. The paste prepared was more than adequate for a single treatment application.

The paste of the present invention is applied as a layer to the epithelial tumor generated by the viral infection, preferably about 1.5 mm in thickness upon the skin or epidermis. Effective application layers, however, can range from about 0.8 mm in thickness up to as much as 10.0 mm in thickness. Thinner layers may require additional applications of the paste to provide optimal treatment, whereas extremely thick layers may be difficult to maintain in their adhering relationship with the affected area.

Shortly after the paste is applied, the paste generally begins to dry out, lose its adherence and fall off the infected epidermal area. Preferably, any area from which the paste has dried and fallen off should be recovered with additional paste.

The infected area should remain completely covered with the paste layer for a suitable period of time, preferably about twenty-five to thirty minutes per treatment. At the end of a treatment period, any remaining paste may be lightly brushed or abraded off of the skin. The treated skin area may then be gently cleansed with water, which tends to remove any remaining paste residue.

The treatment should be persistently performed about one or about two times per day until the periphery of the epithelial tumor begins to separate from the surrounding skin tissue. Subsequent bi-daily treatments of the paste should then be forced in the area separating the tumor and the surrounding skin tissue until the root systems associated with the epithelial tumor turn black, the tumor completely separates from the surrounding skin, and the root systems completely disappear.

EXAMPLE 1

Test subject A, a female caucasian, approximately thirty-six years of age, was treated for a common wart on the little finger of her left hand. The wart was about 0.25 inch (6.4 mm) in diameter and about 0.06 (1.5 mm) inch in height from the surface of the surrounding skin.

The treatment method of this invention was administered during about a one week period. Each treatment session, the paste of this invention was applied to the wart in a layer ranging in thickness from about 0.03 to about 0.06 inch (0.8 to about 1.5 mm) and maintained on the wart for about 20-25 minutes.

A first paste application was made on the first day of treatment. The following day, no noticeable changes in the wart were apparent. A second paste application was made on the third day of the treatment period, with no perceptible changes in the wart's appearance. On the fourth day, however, the periphery of the wart noticeably began to separate from the surrounding skin tissue; the edges of the wart appeared dry. The paste was applied for a third time on the fifth day of the treatment period, with additional paste being worked under the loosened edges of the wart. A more pronounced separation was apparent between the edges of the wart and the surrounding skin tissue.

On the sixth day of the treatment period, a black dot was noticed below the wart's surface at the center of the wart. The surface of the wart appeared somewhat opaque. On the following day (day 7), the wart fell off the test subject, leaving a small hole about 0.06 inch (1.5 mm) in diameter and about 0.02 inch (0.5 mm) deep. All other evidences of a wart appeared to be gone. Upon further inspection approximately two weeks later, the small hole had completely healed. The test subject experienced no ill effects during or after the treatment period.

EXAMPLE 2

Test subject B, a male caucasian, approximately fifty-six years of age, was treated for a small, painful wart on the subject's left elbow. The wart was about 0.2 inch (5.1 mm) in diameter and about 0.06 inch (1.5 mm) in height from the surrounding skin tissue.

The treatment method of this invention was administered during about a seventeen day period. Each treatment session, the paste of this invention was applied to the wart in a layer ranging in thickness from about 0.03 to about 0.06 inch (0.8 to about 1.5 mm) and maintained on the wart for about 30 minutes.

The first three paste applications were administered on the first, third and fourth days of the treatment period, respectively, with no noticeable changes in the appearance of the wart. A fourth paste application was made on the seventh day of the treatment period. Following the fourth treatment session, the surface of the wart appeared to be somewhat dry. A fifth paste application was made on the tenth day of the treatment period, again with a noticeable dryness of the wart's surface following the treatment session.

On the eleventh day of the treatment period, the edges of the wart began to separate from the surrounding skin tissue. A sixth paste application was then made, with additional paste being forced into the areas of separation.

A seventh paste application was made on the twelfth day of the treatment period, again with additional paste being forced into the areas of separation. The surface and edges of the wart appeared hard and dry and a small black dot was apparent beneath the surface of the wart near its center. On the fifteenth day of the treatment period, upon inspection, the edges of the wart were fully separated from the surrounding skin tissue; the only apparent point of attachment for the wart was the blackened root system. Following this inspection, an eighth paste application was made.

On the seventeenth day of the treatment period, while picking at the edges of the wart, the entire wart and its blackened root system was extracted. The root system, which appeared to be about 0.03 inch (0.8 mm) in diameter and about 0.25 inch (6.4 mm) long, remained attached to the wart. A hole resulted in the skin tissue of the elbow that approximated the dimensions of the extracted root system. About seventeen days after this extraction occurred, the skin of the elbow had completely healed except for a tiny scab. Some two and one half years after the conclusion of the treatment period, the elbow remained free from any recurrence of the wart and its associated pain.

EXAMPLE 3

Test subject C, a male caucasian, approximately eleven years in age, who was genetically related to subject B, was treated for a colony of four planter warts located on the ball of the left foot. The wart colony ranged in size from about 0.4 to about 0.5 inch (10.3 to about 12.8 mm) in diameter and about 0.03 to about 0.06 inch (0.8 to about 1.5 mm) in height from the surrounding skin tissue. The subject was experiencing acute pain in the infected area, which resulted in walking difficulty.

The treatment method of this invention was administered during about a thirty day period. During each treatment session, the paste of this invention was applied to the wart colony in a layer ranging in thickness from about 0.03 to about 0.06 inch (0.8 to about 1.5 mm) and maintained on the wart for about 25-30 minutes.

First and second paste treatments were applied on the first day of the treatment period. The first treatment, administered early in the day, was maintained on the infected area for only 10 minutes; the second treatment, administered in the evening, was maintained on the infected area for the entire suggested treatment session duration of about 25-30 minutes. Thereafter, on the subsequent three days of the treatment period, a third, fourth and fifth paste treatment was administered, respectively, with no noticeable changes to the wart colony. On the fifth day of the treatment period, however, following a sixth paste application, the subject noticed that the pain in the infected area had markedly diminished. Four additional treatment sessions were conducted on the seventh, ninth, eleventh and fifteenth days of the treatment period, respectively. Throughout this phase of the treatment period the test subject experienced no pain whatsoever in the infected area.

On the twentieth day of the treatment period, a noticeable separation between the periphery of the coalesced wart colony and the surrounding skin tissue was evidenced. A black dot also was apparent near the center of the wart colony beneath the surface of the skin. An eleventh paste treatment was then administered with additional paste being forced into the area of separation. Similarly, a twelfth paste treatment was likewise applied on the twenty-second day of the treatment period; additional paste was forced into the area of separation.

By the twenty-fifth day of the treatment period a portion of the wart colony had completely separated from the surrounding skin tissue, exposing a black, yet still attached, multi-root system. Another portion of the colony, while still attached to the surrounding skin tissue, had loosened considerably; the central multi-root system had turned a more pronounced black color. A thirteenth application of the paste was administered. Following this treatment session, the test subject soaked the infected foot in a solution of soapy water for about fifteen minutes. At the conclusion of the soaking, the root system from the completely separated portion of the colony had itself become completely separated. The test subject still was free from any pain in the infected area.

No further paste treatments were applied after the twenty-fifth day of the treatment period. Upon further inspection on the thirtieth day of the treatment period, the entire wart colony had been removed along with a major portion of its extensive root system; a small blackened region was still visible. Small holes remained in the formerly infected skin approximating the size and area occupied by the root system. The test subject continued to experience no pain. Thirty-four days after treatment of the infected area began, the small blackened region had disappeared and the skin surface was almost totally healed, as viewed under magnification. The test subject has not experienced any recurrence of the warts and their symptoms.

Conclusion

The method of this invention is an effective treatment for the complete, permanent and painless removal of epithelia tumors caused by the papova-type virus. The method of this invention is an especially effective non-surgical means for treating coalesced epithelial tumor colonies, such as a plantar wart mosaic. Concomitantly, the treatment method of this invention, while arresting the viral infection, alleviates pain associated with epithelial tumors such as plantar warts.

The components required to prepare the pharmaceutical paste of this invention may be conveniently supplied as a kit. Specifically, such a kit would contain a portion of powdered acetylsalicylic acid. Preferably, a portion of distilled water or other suitable water would also be included in the kit. At least one of the portions of the components would be contained in a container suitable for mixing the two components into a paste. Preferably, the kit of this invention would further include instructions for the preparation of the pharmaceutical paste and the procedure for effective treatment of the infected area.

Although the present invention has been described with reference to preferred embodiments, workers skilled in the art will recognize that changes may be made in form and detail without departing from the spirit and scope of the invention.

What is claimed is:

1. A method for treating a body surface infection of a papova-type viral epithelial tumor, the method comprising:
   applying an effective amount of a paste containing acetylsalicylic acid and water in a layer having a thickness of between about 0.8 mm and 10.0 mm over epithelial tumor; and
   maintaining the paste in contact with the epithelial tumor for a treatment period sufficient to affect the infection.

2. The method of claim 1 wherein the epithelial tumor is a plantar wart.

3. The method of claim 1 wherein the treatment period is between about 25 and about 30 minutes.

4. The method of claim 3 and further comprising:
   removing the paste from the epithelial tumor after the treatment period is complete.

5. The method of claim 4 wherein the removing comprises:
   permitting the paste to dry; and
   brushing the dried paste off the epithelial tumor.

6. The method of claim 5 wherein removing further comprises:
   cleaning the epithelial tumor with water to remove any paste residue.

7. The method of claim 6 and further comprising:
   periodically repeating the applying and maintaining steps a number of times until a periphery of the epithelial tumor separates from surrounding skin tissue.

8. The method of claim 7 and further comprising:
   directing the paste beneath the periphery of the epithelial tumor and the separating skin tissue until a root system of the epithelial tumor turns black, evidencing the demise of the viral infection.

9. The method of claim wherein the paste contains acetylsalicylic acid and water in proportions of about 1.63:1.00 to about 0.26:1.00.

10. A method for treating a papova-type viral infection of a body surface and an associated epithelial tumor, the method comprising:
    covering the epithelial tumor with a layer, having a thickness of between about 0.8 mm and 10.0 mm, of an effective amount of a paste containing as an active ingredient acetylsalicylic acid in a concentration sufficient to arrest the papova-type viral infection; and
    maintaining the paste in contact with the epithelial tumor for a treatment period of up to about thirty minutes; and
    repeating the covering and maintaining steps until the viral infection is arrested.

11. The method of claim 10 wherein the epithelial tumor is a plantar wart.

12. The method of claim 10 wherein the paste consists essentially of acetylsalicylic acid and water.

13. The method of claim 10 wherein the proportion of the acetylsalicylic acid and the water is about 1.63:1.00 to about 0.26:1.00.

14. The method of claim 10 wherein the treatment period is at least about 25 minutes.

15. The method of claim 10 and further comprising:
    permitting the paste to dry; and
    brushing the dried paste off the epithelial tumor.

16. The method of claim 15 and further comprising:
    cleansing the affected area with water to remove any paste residue.

17. The method of claim 10 and further comprising:
    periodically repeating the covering and
    maintaining steps a number of times until a periphery of the epithelial tumor separates from surrounding skin tissue.

18. The method of claim 17 and further comprising:
    directing the paste into an area of separation between the periphery of the epithelial tumor and the surrounding skin tissue until a root system of the epithelial tumor turns black, evidencing the demise of the viral infection.

19. A method for treating a body surface infection of a coalesced papova-type viral epithelial tumor colony, the method comprising:
    applying an effective amount of a paste containing acetylsalicylic acid and water to cover the entire infected surface area with a layer having a thickness of between about 0.8 mm and 10.0 mm; and
    maintaining the paste in contact with the entire infected surface area for a treatment period sufficient to affect the infection.

20. The method of claim 19 wherein the coalesced colony of epithelial tumors includes plantar warts.

21. The method of claim 19 wherein the treatment period is between about 25 and 30 minutes.

22. The method of claim 21 and further comprising:
    removing the paste from the entire infected area after the treatment period is complete.

23. The method of claim 22 wherein the removing comprises:
    permitting the paste to dry; and
    brushing the dried paste off the entire infected area.

24. The method of claim 23 wherein removing further comprises:
    cleaning the entire infected area with water to remove any paste residue.

25. The method of claim 24 and further comprising:
    periodically repeating the applying, covering and maintaining steps a number of times until a periphery of each epithelial tumor separates from surrounding skin tissue.

26. The method of claim 25 and further comprising:
    directing the paste beneath the periphery of each epithelial tumor and the separating skin tissue until a root system of each epithelial tumor turns black, evidencing the demise of each viral infection.

27. The method of claim 19 wherein the paste contains acetylsalicylic acid and water in proportions of about 1.63:1.00 to about 0.26:1.00.

* * * * *

UNITED STATES PATENT AND TRADEMARK OFFICE
CERTIFICATE OF CORRECTION

PATENT NO. : 5,151,415

DATED : September 29, 1992

INVENTOR(S) : DALLAS SIRANY

It is certified that error appears in the above-identified patent and that said Letters Patent is hereby corrected as shown below:

Col. 7, line 61, delete "claim", insert "claim 1"

Signed and Sealed this

Twenty-first Day of September, 1993

Attest:

BRUCE LEHMAN

*Attesting Officer*  *Commissioner of Patents and Trademarks*